(12) United States Patent
Knight et al.

(10) Patent No.: US 9,592,102 B2
(45) Date of Patent: Mar. 14, 2017

(54) DENTAL HAND TOOL WITH DISINFECTION REACTOR

(75) Inventors: Douglas Gordon Knight, London (CA); Nathan Hemmer, Rock Hill, SC (US)

(73) Assignee: KaVo Dental Technologies, LLC, Lake Zurich, IL (US)

( * ) Notice: Subject to any disclaimer, the term of this patent is extended or adjusted under 35 U.S.C. 154(b) by 624 days.

(21) Appl. No.: 12/542,001

(22) Filed: Aug. 17, 2009

(65) Prior Publication Data

US 2010/0291502 A1 Nov. 18, 2010

Related U.S. Application Data

(60) Provisional application No. 61/179,229, filed on May 18, 2009.

(51) Int. Cl.
*A61C 17/02* (2006.01)
*C02F 1/32* (2006.01)
*A61C 1/00* (2006.01)

(52) U.S. Cl.
CPC ........ *A61C 1/0076* (2013.01); *A61C 17/0202* (2013.01); *C02F 1/32* (2013.01)

(58) Field of Classification Search
CPC .................. A61C 1/0076; A61C 17/0202
USPC ......................................................... 250/435
See application file for complete search history.

(56) References Cited

U.S. PATENT DOCUMENTS

| | | | | |
|---|---|---|---|---|
| 5,476,379 A | * | 12/1995 | Disel ........................ | A61C 1/18 433/126 |
| 5,635,133 A | * | 6/1997 | Glazman ........................ | 422/24 |
| 5,749,726 A | * | 5/1998 | Kinsel .................. | A61C 1/0076 433/126 |
| 6,042,377 A | * | 3/2000 | Ito ................................. | 433/126 |

(Continued)

FOREIGN PATENT DOCUMENTS

| | | |
|---|---|---|
| JP | 05-031157 | 1/1993 |
| JP | 2006280831 | 10/2006 |

(Continued)

*Primary Examiner* — Robert Kim
*Assistant Examiner* — Eliza Osenbaugh-Stewar
(74) *Attorney, Agent, or Firm* — Timothy H. Van Dyke; Beusse, Wolter, Sanks & Maire, PLLC

(57) ABSTRACT

A dental hand tool including a main body having a main body proximate end, a main body distal end, at least one dental utility conduit associated with the main body proximate end, and a dental disinfection system associated with the main body that disinfects dental fluid at a point of use. The dental disinfection system includes a disinfection reactor associated with the main body, a collimated germicidal UV light source end, a disinfection reactor distal end, disinfection reactor walls, a disinfection reactor fluid inlet that receives the dental fluid from a dental fluid source, a disinfection reactor dental fluid outlet that delivers the dental fluid to the point of use, and a disinfection reactor inner chamber. The collimated germicidal UV light source end directs collimated germicidal UV light toward the disinfection reactor distal end along a collimated germicidal UV light path that is substantially perpendicular to the disinfection reactor distal end, and substantially parallel to the disinfection reactor walls, such that germicidal UV light substantially fills the disinfection reactor inner chamber.

23 Claims, 4 Drawing Sheets

(56) References Cited

U.S. PATENT DOCUMENTS

| | | |
|---|---|---|
| 6,268,607 B1 | 7/2001 | Marsh et al. |
| 6,740,244 B2 * | 5/2004 | Baca .................... A61C 1/0046 210/748.06 |
| 6,766,097 B2 | 7/2004 | Horton, III |
| 6,773,610 B2 | 8/2004 | Korin |
| 7,160,370 B2 * | 1/2007 | Baca et al. ...................... 96/224 |
| 7,411,200 B2 | 8/2008 | Park et al. |
| 2002/0079271 A1 | 6/2002 | Baca |
| 2005/0173352 A1 * | 8/2005 | Burrows et al. .............. 210/748 |
| 2006/0147339 A1 | 7/2006 | Hunter |
| 2006/0163126 A1 * | 7/2006 | Maiden ........................... 210/87 |
| 2007/0256962 A1 * | 11/2007 | Larsson ........................ 210/85 |
| 2008/0055521 A1 * | 3/2008 | Mizutani et al. .............. 349/96 |
| 2009/0026385 A1 | 1/2009 | Knight |

FOREIGN PATENT DOCUMENTS

| | | |
|---|---|---|
| WO | WO2004/011038 | 2/2004 |
| WO | WO/2004/028290 | 8/2004 |

* cited by examiner

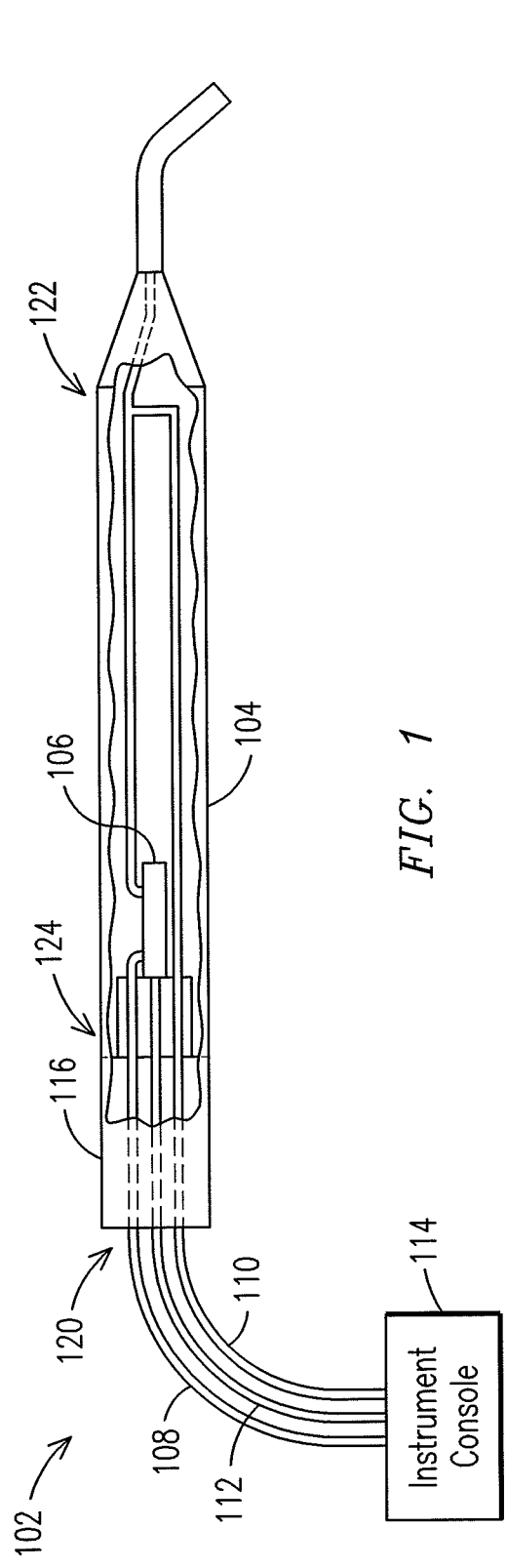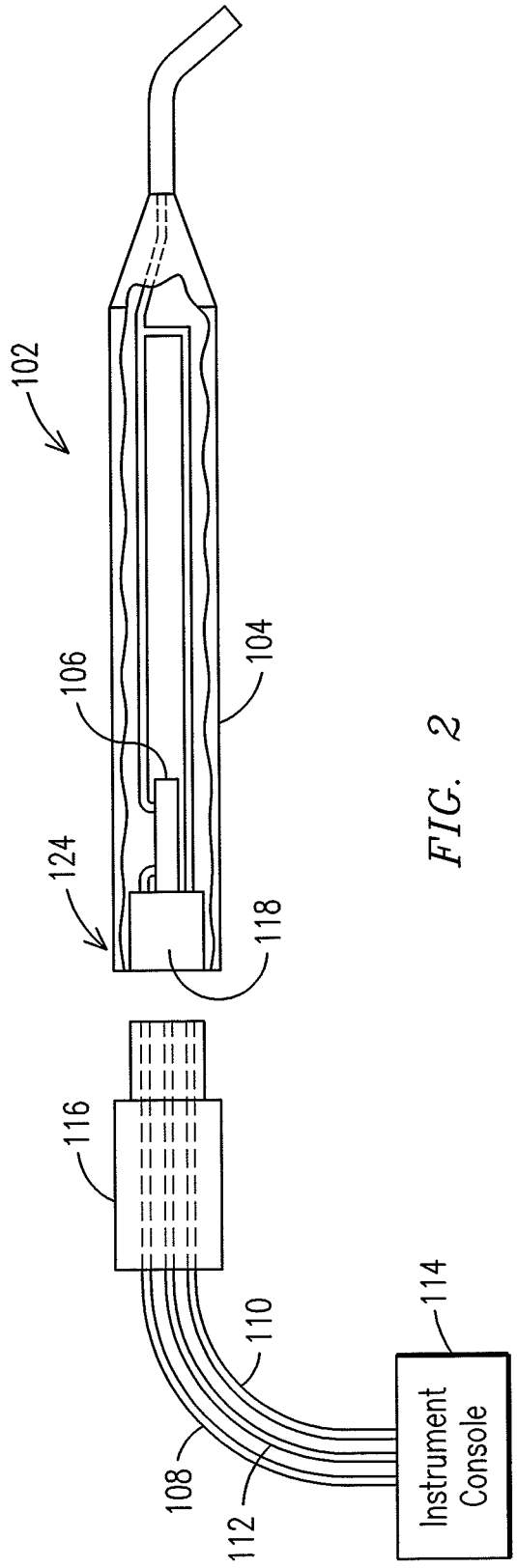

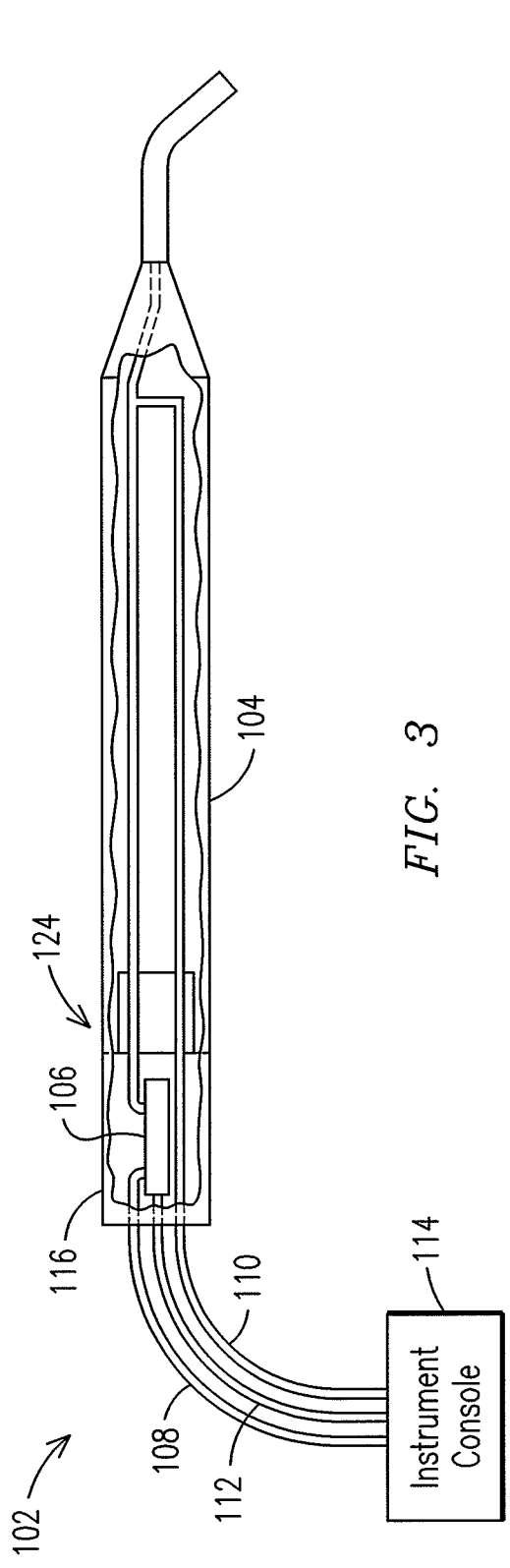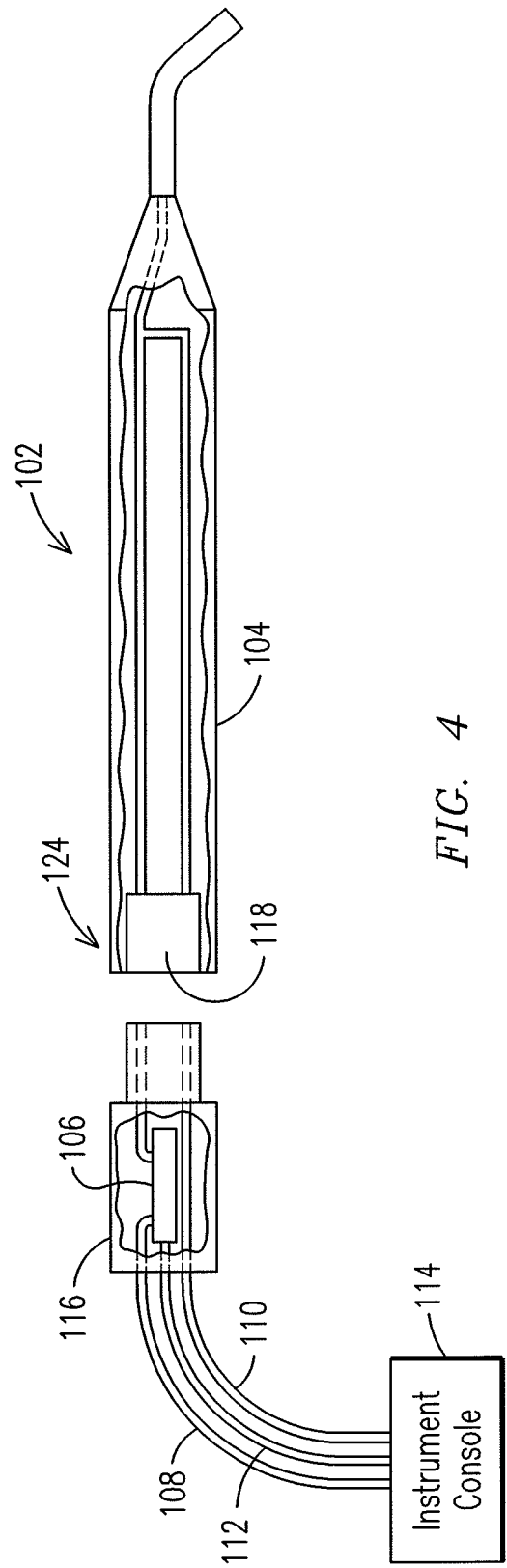

DENTAL HAND TOOL WITH DISINFECTION REACTOR

RELATED APPLICATIONS

This application claims priority to U.S. Ser. No. 61/179,229 filed May 18, 2009, which is incorporated herein it its entirety.

FIELD OF THE INVENTION

This invention relates to the use of UV light to disinfect fluids in a dental operatory. It is particularly directed toward a disinfection reactor that disinfects fluids at the dental hand tool.

BACKGROUND

Dental hand tools often require fluids to operate. In particular, water can be used to cool a dental tool, as well as to irrigate a patient's mouth. Water can be supplied to the dental tool via a flexible conduit, such as a tube, that is connected to the hand tool at one end, and an instrument console at another end. Due to the nature of the work being performed in the patient's mouth, any water that enters the patient's mouth must be free from pathogens that might cause an infection. Accordingly, the U.S. Center for Disease Control ("CDC") recommends that the number of bacteria in water used as a coolant/irrigant for nonsurgical dental procedures should have an aerobic heterotropic plate count ("HPC") of ≤500 colony forming units ("CFU")/ml. This number was selected based on a recommendation for levels of HPC in potable water. In addressing this issue, the American Dental Association ("ADA") has proposed that water used in dental treatment contain a bacterial level of ≤200 CFU/ml. E. W. Rice, W. K. Rich, C. H. Johnson, and D. J. Lye, "The Role of Flushing Dental Water Lines for the Removal of Microbial Contaminants", Public Health Rep. May-June 2006; 121(3): 270-274. HPC counts as high as ~30,000 CFU/ml have been detected for dental supply systems with no disinfection precautions, and other precautions such as flushing of the lines still results in HPC counts above the recommended values. Pathogens such as *Pseudomonas, Klebsiella, Legionella*, and non-tuberculosis *Mycobacterium* species have been detected in water from dental supply lines. H. S. Bednarsh, K. J. Eklund, and S. Mills, "Dental Unit Waterlines: Check Your Dental Water Unit IQ", Access Vol. 10, No. 9, copyright ©1997 by the American Dental Hygienists' Association. *Pseudomonas* is a well-known opportunistic pathogen and a common contaminant in dental unit water.

Several techniques for treating dental fluids have been developed because of the pathogens that have been found in the dental fluids. One method includes installing a UV disinfection unit in the instrument console, to treat the fluid in the console. Chemical treatment of the supply lines, for example chlorine or ozone, has been used. Microbial filters have also been installed at the dental hand tool to treat the dental fluid as it enters the hand tool.

BRIEF DESCRIPTION OF THE DRAWINGS

The invention is explained in the following description in view of the drawings that show:

FIG. 1 is a side view of a dental hand tool with an embodiment of the disinfection system of the present invention where the disinfection reactor is located in the hand tool.

FIG. 2 is a side view of the dental hand tool with the disinfection system of FIG. 1, where the dental utility supply conduit connector has been disconnected from the hand tool.

FIG. 3 is a side view of a dental hand tool embodiment comprising a disinfection system with a reactor where the disinfection reactor is located in dental utility supply conduit connector.

FIG. 4 is a side view of the dental hand tool with a disinfection system as shown in FIG. 3, where the dental utility supply conduit connector has been disconnected from the hand tool.

DETAILED DESCRIPTION

Figure 5:
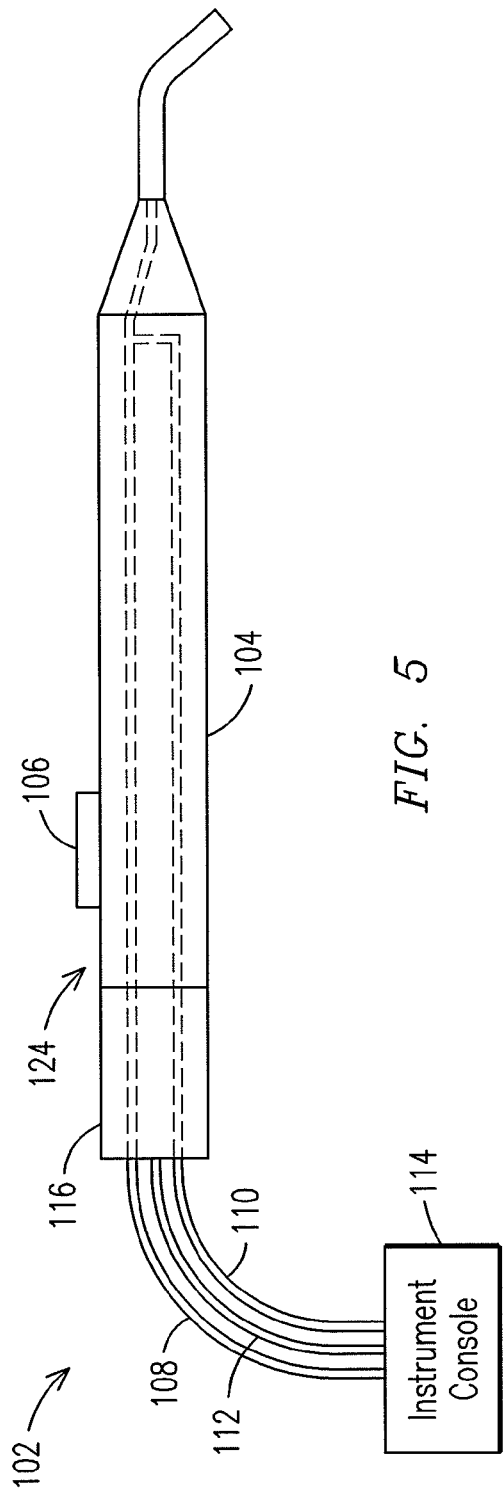
FIG. 5 is a side view of a dental hand tool embodiment comprising a disinfection system with a reactor, where the disinfection reactor is attached to the dental hand tool.

Disinfecting dental fluids at the instrument console supplies disinfected fluid to the dental utility supply line, but that fluid must travel through a length of dental utility supply line, and then through the dental hand tool, before entering the patient's mouth. Dental utility supply line, commonly tubing, often has a very large surface area, and the dental fluid flows at a slow rate. This provides an ideal environment for the buildup of microbial colonies on the inner surfaces of the dental utility supply line, which can result in large concentrations of microbes in the water that flows to the dental hand tool. Thus, although the dental fluid has been disinfected at the instrument console, it may become contaminated with pathogens on the way to the patient's mouth, possibly resulting in an infection. Accordingly, the inventors have identified a problem that to their knowledge has not previously been recognized and/or addressed. The inventors have developed dental hand tools and/or components associated with such tools that ensure that infection and delivery of microbial contaminants are minimized at the downstream end of the dental fluid supply. In conjunction with the implementation of a dental hand tool having a disinfection system that disinfects proximate to the point of use, the inventors have developed a unique miniaturized disinfection reactor that, while small enough to be implemented in an attachment adjacent to the dental tool or even within the dental tool itself, is capable of disinfecting passing fluid. The size and operation of the disinfection reactor enables disinfection of the fluid supply without impeding the operation and manipulation of the dental tool itself.

According to one embodiment, a disinfection reactor is positioned at the downstream end of the dental utility supply conduit, either in a connector at the downstream end of the dental utility supply conduit, or in the dental hand tool itself. Consequently, disinfection occurs when the dental fluid enters the upstream end of the dental hand tool, which is very close to the actual point of use, defined as the downstream end of the dental utility supply conduit. As a result, in this unique system, any pathogens that are picked up by the dental fluid as it travels through the dental supply conduit are still subject to the disinfection procedure before reaching the point of use. The distance between the disinfection reactor of the present invention and the point of use, is approximately the length of the dental hand tool itself. This distance is minimal when compared to the distance between the disinfection reactor of the prior art, located in the instrument console, as opposed to the point of use. As a result, the possibility that the dental fluid would pick up any pathogens between the disinfection reactor and the point of use is greatly reduced with the present invention. In systems where there is a microbial filter at the dental hand tool, this innovative solution eliminates the need for replacing filters.

As stated above, the inventors have developed a disinfection reactor that is unique in the sense that it is small yet effective to kill pathogens potentially present in the fluid supply. Moreover, the disinfection reactor provides effective disinfection without a disruption in the fluid flow and supply. Because of the disinfection potential and small size, the disinfection chamber is able to address the problem of potential pathogen infection not addressed by prior art dental disinfection chambers, by placement proximate to the point of use. In a specific embodiment, the disinfection reactor has a reaction chamber and implements a germicidal UV light source that is positioned to deliver disinfecting light in an efficient manner within the chamber. The reactor is able to collimate the light and direct the collimated light into the reaction chamber to increase the germicidal effectiveness of the light. This facilitates disinfection in a reactor of a small enough size that is practical for a dental hand tool, while at the same time, not significantly impeding the flow of fluid through the tool to the point of use.

Prior art dental fluid disinfection used mercury lamps to produce germicidal UV radiation. Mercury lamps are extremely bulky and require high voltages, typically >100V, to ignite the lamp. These lamps require high operating voltages and present a potential safety hazard to the dentist and patient. Chemical disinfection of the supply lines can produce disinfection byproducts which may be harmful to patients if swallowed, necessitating diligence on the part of the individual performing the treatment. Further, such treatments may degrade the dental utility supply line through a chemical reaction with the disinfectant and the supply line material, shortening the life of the supply line, thereby increasing operational costs. The possibility of using microbial filters at the dental hand tool would require the daily removal and installation of new filters, which expends valuable time and increases operation costs as well.

Embodiments of the invention overcome these issues and concerns related to other possible dental disinfection systems.

Moreover, conventional disinfection systems typically involve a central disinfection and/or filter unit stationed in one location in a dental office. This system is located upstream from the delivery units in the office, and as such, is the only source of disinfection of the water for all of the delivery units in the office. Should the central unit ever malfunction, this would result in either having to shut down dental operations throughout the entire dental office; or if the malfunction is unknown, this would cause the delivery of tainted water to each of the delivery units in the dental office, thereby creating the danger of microbial exposure to patients. Having a disinfection reactor proximate to point of use avoids each of these potential problems. Furthermore, in specific embodiments, the dental instrument gives a visual and/or auditory indication of whether the disinfection reactor is functioning. In the event that the disinfection reactor has a problem, the operator will immediately know this and can cease operation. Unlike for conventional disinfection systems, the operator can simply transfer to another dental operatory having a dental instrument with disinfection reactor. This results in minimal interruption of dental operations, while the malfunctioning dental instrument can be fixed or replaced.

In a related embodiment, the dental hand tool with the associated disinfection reactor includes an indicator light enabling the operator know whether the disinfection reactor is working. Alternatively, since the disinfection reactor utilizes ultraviolet light, a phosphor which emits visible light when exposed to ultraviolet light can be placed within the disinfection reactor. A window or other space is provided to allow the visible light to escape the disinfection reactor such that the visible light produced by the presence of UV light is visible to the operator. If the light is not being shown, the operator will know that the reactor is not functioning.

There are certain industry and regulatory guidelines as to the proper treatment of water used for dental operations. The regulatory guidelines vary from region to region, but they generally require the use of either a central disinfection unit having a UV arc type light or set forth protocols for chemical disinfection. Attempting to address the issue of contamination and biofilms in the water supply lines by chemical treatments presents several drawbacks. Chemical treatments are harsh to the supply line and other equipment, which leads to premature wear on the equipment, resulting in costly and time consuming replacement and/or repair of equipment. Furthermore, various disinfection agents and water additives react with organic and inorganic materials within a distribution system generating by-products that make the water supply no longer potable. Such chemical treatments require time-consuming flushing of the system and testing of the water to ensure that harmful chemical components have been removed from the water supply line and other parts of the system.

Depending on the governing regulations for a particular region, dental hand tool embodiments of the invention could in most cases supplant all of the disinfection systems that a dental office is implementing. For example, implementation of the dental hand tool embodiments could enable the dental office to essentially shut down their present disinfection system, thereby significantly reducing the cost and time required for maintaining such systems. Naturally, this could be achieved in a setting where the dental instrumentation is replaced with dental hand tool embodiments of the present invention or retrofitting of disinfection reactors onto the dental instrumentation.

In one embodiment, the invention pertains to a dental hand tool including a main body having a main body proximate end, a main body distal end, at least one dental utility conduit associated with the main body proximate end, and a dental disinfection system associated with the main body that disinfects dental fluid at a point of use. The dental disinfection system includes a disinfection reactor associated with the main body, a germicidal light source end, a disinfection reactor distal end, disinfection reactor walls, a disinfection reactor fluid inlet that receives the dental fluid from a dental fluid source, a disinfection reactor dental fluid outlet that delivers the dental fluid to the point of use, and a disinfection reactor inner chamber. The germicidal light source end preferably uses a UV light emitting diode (LED) as a UV light source and may be collimated to improve efficiency. See US Patent Publication No. 20090026385 for background on LED light sources. The germicidal light source end directs germicidal light toward the disinfection reactor distal end along a germicidal light path that is substantially perpendicular to the disinfection reactor distal end, and substantially parallel to the disinfection reactor walls, such that germicidal light substantially fills the disinfection reactor inner chamber.

As noted above, the germicidal light may take the form of a collimated LED UV light source. Though collimated light is preferred, this is not imperative. For example, the reactor could include two or more non-collimated LED (or other type) light sources situated at different locations of the reactor. The multiple light sources would compensate for the lack of germicidal effectiveness achieved by collimation. This multi-source arrangement would be less efficient but could nonetheless provide effective disinfection. In another embodiment there is a dental hand tool including a main body having a main body proximate end, a main body distal end, at least one dental utility conduit associated with the main body proximate end, and a dental disinfection system associated with the main body that disinfects dental fluid at a point of use, where the point of use is proximate the main body distal end. The dental disinfection system includes a disinfection reactor positioned at least substantially within the main body, including a collimated germicidal UV light source end, a disinfection reactor distal end, disinfection reactor walls, a disinfection reactor dental fluid inlet that receives the dental fluid from a dental fluid source, a disinfection reactor dental fluid outlet that delivers the dental fluid to the point of use, and a disinfection reactor inner chamber. The collimated germicidal UV light source end further directs collimated germicidal UV light toward the disinfection reactor distal end along a collimated germicidal UV light path that is substantially perpendicular to the disinfection reactor distal end, and substantially parallel to the disinfection reactor walls, such that germicidal UV light substantially fills the disinfection reactor inner chamber.

In another embodiment, there is a dental delivery system including a dental utility conduit, a dental utility conduit connector, a dental hand tool proximate end, a main body distal end, and a dental disinfection system that disinfects dental fluid at a point of use wherein the point of use is proximate a dental hand tool distal end. The disinfection system is small enough for implementation within, on or just upstream of the dental tool without impeding the operation or hand manipulation of the dental tool. In a specific embodiment, the dental disinfection system includes a disinfection reactor positioned at least substantially within the dental utility conduit connector, including a germicidal UV light source end, a disinfection reactor distal end, disinfection reactor walls, a disinfection reactor dental fluid inlet that receives the dental fluid from the dental utility conduit, a disinfection reactor dental fluid outlet that delivers the dental fluid to the dental hand tool proximate end, and a disinfection reactor inner chamber. The germicidal UV light source end further directs germicidal UV light toward the disinfection reactor distal end along a germicidal UV light path that is substantially perpendicular to the disinfection reactor distal end, and substantially parallel to the disinfection reactor walls, such that germicidal UV light substantially fills the disinfection reactor inner chamber.

In a more specific embodiment, the dental hand tool or dental utility conduit connector includes a disinfection reactor including a germicidal UV light source end, a disinfection reactor distal end, disinfection reactor walls, a disinfection reactor fluid inlet that receives the dental fluid from a dental fluid source, a disinfection reactor dental fluid outlet that delivers the dental fluid to the point of use, and a disinfection reactor inner chamber. The germicidal UV light source end may include a wide angle germicidal UV light emitting diode, and a quartz collimating lens. The germicidal UV light source end may include a wide angle germicidal UV light emitting diode, a germicidal UV light emitting diode power source, a parabolic reflector, and a germicidal UV light transparent plate.

Alternatively, the germicidal UV light source end comprises a narrow angle germicidal UV light emitting diode emitting collimated germicidal UV light. The germicidal UV light source end may further include a germicidal UV light transparent plate between the narrow angle germicidal UV light emitting diode and the disinfection reactor. The germicidal UV light source end may further include a germicidal UV light transparent quartz lens between the narrow angle germicidal UV light emitting diode and the disinfection reactor.

Turning to the drawings, FIG. 1 depicts a UV LED disinfection system 102, a dental hand tool 104, and an instrument console 114. The UV LED disinfection system 102 includes an a dental utility supply conduit 108, an optional dental utility return conduit 110, an LED power and control conduit 112, a dental utility conduit connector 116, and a UV LED disinfection reactor 106. It can be seen that dental utility supply conduit 108 delivers dental fluid (not shown), typically water, from the instrument console 114 to the dental hand tool 104. A dental utility conduit connector 116 is connected to the dental utility supply conduit 108 at a dental utility supply conduit downstream end 120, and the dental utility conduit connector 116 connects the dental utility supply conduit 108 to a dental hand tool proximate end 124. Dental fluid travels through the dental utility supply conduit 108 and into the disinfection reactor 106 where it is disinfected. The dental fluid then may continue through the dental hand tool 104 to cool it, and then return to the instrument console 114 via dental utility return conduit 110. The dental fluid may alternately continue through the dental hand tool 104 until it reaches the dental hand tool downstream end 122, where it may exit the dental hand tool 104 into a patient's mouth or other point of use. Thus, it can be seen that disinfection occurs at the dental hand tool 104, reducing any concern about any pathogens that may be picked up by the dental fluid as it travels to the dental hand tool 104.

FIG. 2 shows the UV LED disinfection system 102, dental hand tool 104, and disinfection reactor 106 of FIG. 1, where the dental utility conduit connector 116 has been disconnected from a proximate end 124 of the dental hand tool 104, revealing dental hand tool connector recess 118.

FIG. 3 shown an embodiment of the UV LED disinfection system 102 where the disinfection reactor 106 is located in the dental utility conduit connector 116, as opposed to being located in the dental hand tool 104. In this embodiment, dental utility conduit connector 116 connects dental utility supply conduit 108 to the dental hand tool proximate end 124 in the same manner as before. The difference is that the disinfection reactor 106 is located in the dental utility conduit connector 116, yielding the advantage that there need be only a single disinfection reactor 106 to serve a multitude of dental hand tools compatible with dental utility conduit connector 116.

FIG. 4 shows the UV LED disinfection system 102, dental hand tool 104, and disinfection reactor 106 of FIG. 3, where the dental utility conduit connector 116 has been disconnected from a proximate end 124 of the dental hand tool 104, revealing dental hand tool connector recess 118.

FIG. 5 shown an embodiment of the UV LED disinfection system 102 where the disinfection reactor 106 is attached to the dental hand tool 104. Such an embodiment permits a wide range of positions in which the disinfection reactor 106 can be placed, affording greater freedom in design.

Figure 6:
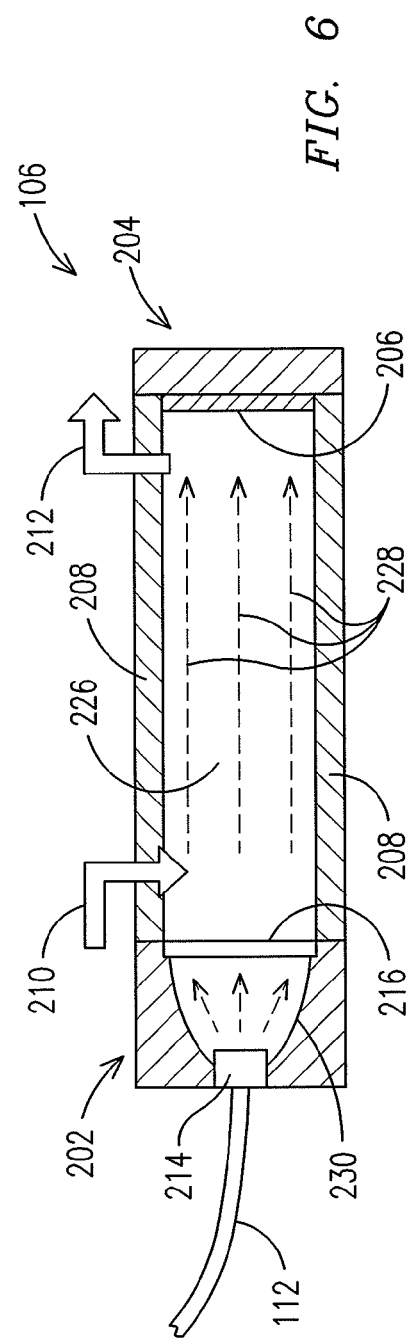
FIG. 6 is a side view of an embodiment of the disinfection system where the source of UV light is an LED located at the disinfection reactor.

FIG. 6 shows the elements of the disinfection reactor 106, including the LED power and control conduit 112 connected to the collimated germicidal UV light source end 202, which forms one end of the disinfection reactor 106. The collimated germicidal UV light source end 202 is connected to the disinfection reactor walls 208, which are connected at the disinfection reactor distal end 204. The collimated germicidal UV light source end 202 and the disinfection reactor distal end 204 may be removably fastened to disinfection reactor walls 208 by, for example, threaded connections, or any other suitable releasable connection. Removable ends will facilitate mechanical cleaning of the disinfection reactor 106, which may experience fouling over a period of use. Alternatively, the ends may be permanently attached. Disinfection reactor fluid inlet 210 permits dental fluid to enter the disinfection reactor 106, and disinfection chamber fluid outlet 212 permits dental fluid to exit the disinfection reactor 106 and proceed to the point of use to cool to dental hand tool 104, and/or to irrigate the patient's mouth etc. The disinfection reactor distal end 204 may have a disinfection reactor distal end reflective surface 206 on an inner side, which will reflect the collimated germicidal UV light 228 emitted at the other end of the disinfection reactor inner chamber 226 by the collimated germicidal UV light source end 202. For example, disinfection reactor distal end reflective surface 206 may be a mirror, or may be a coating of a reflective material, or may simply be a reflective surface of the disinfection reactor distal end 204, such as an aluminum surface, which may further be polished to facilitate reflection of the collimated germicidal UV light 228. Any or all of the collimated germicidal UV light source end 202, disinfection reactor walls 208, and disinfection reactor distal end 204 may be made of material that will conduct heat generated by the disinfection reactor 106 away from the disinfection reactor 106, possibly into the dental fluid. For example, they may be made of aluminum, which would conduct heat away from the source and into the dental fluid. Further, disinfection reactor walls 208 may have a reflective inner surface, either by application of a reflective material, or by polishing of the reflective material of the disinfection reactor walls 208, to further reflect collimated germicidal UV light 228 back into the dental fluid.

In an embodiment, the collimated germicidal UV light source end 202 emits collimated light into a disinfection reactor inner chamber 226 in a direction substantially parallel to the disinfection reactor walls 208, and substantially perpendicular to the disinfection reactor distal end 204, such that collimated germicidal UV light 228 substantially fills the disinfection reactor inner chamber 226. The disinfection reactor 106 may be configured such that the disinfection reactor inner chamber 226 is elongated along the path of the collimated germicidal UV light 228. The collimated germicidal UV light 228 travels through the dental fluid in the disinfection reactor inner chamber 226, disinfecting the dental fluid as it travels through it. When the collimated germicidal UV light 228 reaches the disinfection reactor distal end 204 it may be reflected back by the disinfection reactor distal end reflective surface 206, so that it can increase the intensity of the collimated germicidal UV light 228 in the disinfection reactor inner chamber 226.

In order for the collimated germicidal UV light source end 202 to emit collimated germicidal UV light, the UV light source itself may emit collimated germicidal light, or alternatively, the UV light source may emit non collimated germicidal light, and that non collimated light may subsequently be collimated by another structure within the collimated germicidal UV light source end 202. As a result, whether the germicidal UV light source 214 itself emits collimated or non collimated germicidal UV light, the collimated germicidal UV light source end 202 will emit collimated germicidal UV light into the disinfection reactor inner chamber 226. Thus, the invention permits the collimated germicidal UV light source end 202 to be configured in multiple ways.

In an embodiment, the collimated germicidal UV light source end 202 includes a germicidal UV light source 214 which is a wide angle germicidal UV light emitting diode ("LED"). A wide angle germicidal UV LED emits non collimated germicidal UV LED light. In an embodiment, the non collimated germicidal UV light emitted from the wide angle germicidal UV LED can be substantially collimated using a germicidal UV light transparent plate 216 when that germicidal UV light transparent plate 216 is a quartz collimating lens. Substantially collimated light generally means light that has been collimated to the degree possible using convention techniques of collimating, such as is possible through the use of a parabolic reflector, or a lens. In this embodiment, the quartz collimating lens substantially collimates the non collimated germicidal UV light emitted from the wide angle germicidal UV LED, such that collimated germicidal UV light is emitted from the collimated germicidal UV light source end 202 into the disinfection reactor inner chamber 226. In another embodiment, the non collimated germicidal UV light emitted from the wide angle germicidal UV LED can be substantially collimated using a parabolic reflector 230. The parabolic reflector 230 substantially collimates the non collimated germicidal UV light emitted from the wide angle germicidal UV LED. As a result, germicidal UV light transparent plate 216 can be a quartz plate that simply allows the already collimated germicidal UV light to pass through it into the disinfection reactor inner chamber 226. In another embodiment, the germicidal UV light source 214 can be a narrow angle germicidal UV LED, which is substantially collimated germicidal UV light. Again, germicidal UV light transparent plate 216 can be a quartz plate that simply allows the already collimated germicidal UV light to pass through it into the disinfection reactor inner chamber 226.

It is also contemplated to use a quartz lens as the germicidal UV light transparent plate 216 when the germicidal UV light source 214 emits substantially collimated light, because the quartz lens may increase the amount of collimation of the collimated germicidal UV that exits the collimated germicidal UV light source end 202 and enters the disinfection reactor inner chamber 226. So long as the collimated germicidal UV light source end 202 emits substantially collimated germicidal UV light 228, it is a configuration contemplated by this invention. Embodiments that emit non collimated light are also contemplated should other factors, including, but not limited to, economic manufacture, require such a configuration. Such embodiments could include, but are not limited to, a wide angle germicidal UV LED as the germicidal UV light source 214, where the germicidal UV light transparent plate 216 is a quartz plate. Other combinations are readily ascertainable from this disclosure. However, options that utilize collimated light are preferred because there are fewer losses due to reflection losses of the germicidal UV light as it reflects off the disinfection reactor walls 208. The losses can be due to characteristics of the reflecting surface of the disinfection reactor walls 208, or fouling present on the disinfection reactor walls 208 prevalent when non collimated light is used.

Figure 7:
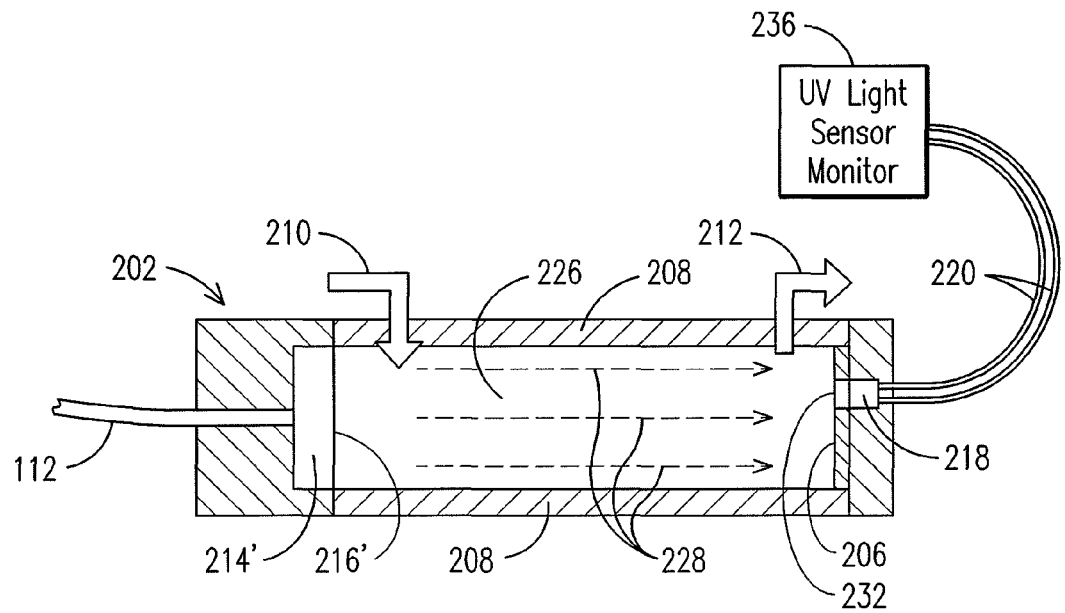
FIG. 7 is a side view of an embodiment of the UV LED disinfection system of the present invention where the source of UV light is an LED array located at the disinfection reactor.

FIG. 7 shows another embodiment of the present invention where the germicidal 214' is a UV LED array that emits narrow angle germicidal UV light. Since the germicidal UV light emitted by the UV LED array is already substantially collimated, the germicidal UV light transparent plate 216' can be a quartz plate that simply allows the already collimated germicidal UV light to pass through it into the disinfection reactor inner chamber 226. Alternatively, there may be no germicidal UV light transparent plate 216', and the UV LED array may emit collimated germicidal UV light directly into the disinfection reactor inner chamber 226. In such an embodiment the UV LED array would be cooled directly by the dental fluid, as well as indirectly by the cooling effects provided by the heat conductive material which the disinfection reactor 106 is made from. Also shown is an optional germicidal UV light sensor 218, controlled and powered by germicidal UV light sensor utility conduits 220 connected to a germicidal UV light sensor monitor 236. The germicidal UV light sensor 218 may be installed in the disinfection reactor distal end 204, behind a disinfection reactor distal end reflective surface sensing window 232 in the disinfection reactor distal end reflective surface 206, so that the germicidal UV light sensor 218 can detect the amount of germicidal UV light that reaches the disinfection reactor distal end 204. The intensity of the collimated germicidal UV light 228 in the disinfection reactor inner chamber 226 can then be monitored by the germicidal UV light sensor monitor 236. This will provide the user with information about whether or not there is sufficient collimated germicidal UV light 228 in the disinfection reactor inner chamber 226 to properly disinfect the dental fluid. If there is not, the user can adjust the intensity of the germicidal UV light source 214, clean the disinfection reactor inner chamber 226, and/or maintain the UV LED disinfection system 102 as necessary.

Figure 8:
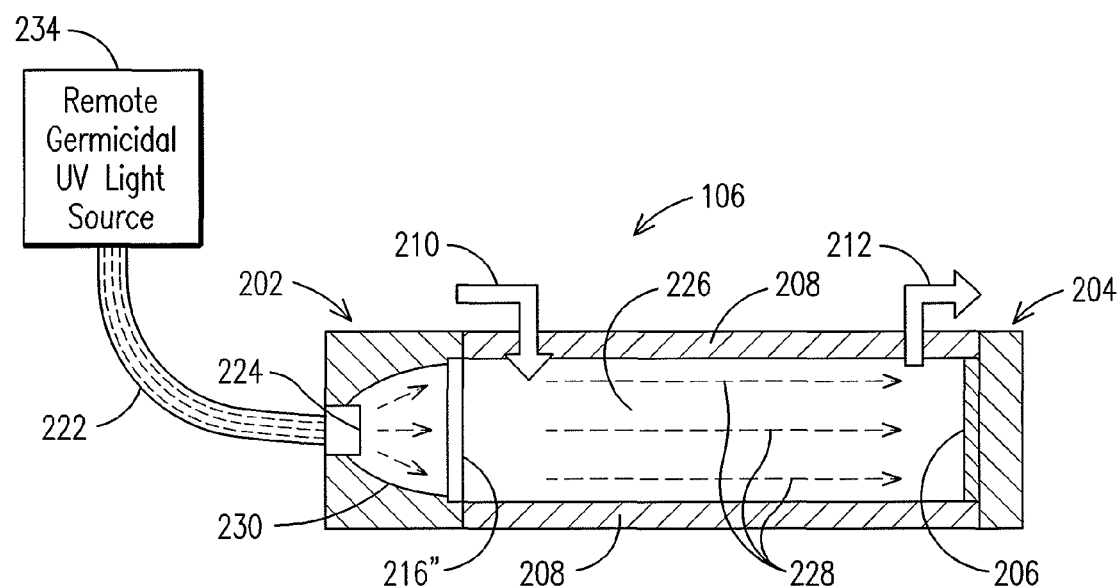
FIG. 8 is a side view of an embodiment of a UV disinfection system of the present invention where the source of UV light is a fiber optic cable delivering UV light to the disinfection reactor from a remote UV light source.

FIG. 8 shows another embodiment where the germicidal UV light source is a system including a remote germicidal UV light source 234 located remote from the collimated germicidal UV light source end 202, a germicidal UV light transmitting fiber optic cable 222 (dashed lines represent individual optic fibers), and a germicidal UV light source transparent window 224 located in the collimated germicidal UV light source end 202. The germicidal UV light transmitting fiber optic cable 222 transmits germicidal UV light from the remote germicidal UV light source 234 to the germicidal UV light source transparent window 224. Depending on its configuration and characteristics, the germicidal UV light source transparent window 224 may emit wide angle (non collimated) germicidal UV light or narrow angle (collimated) light. Germicidal UV light in the remote germicidal UV light source 234 may be generated by at least one germicidal UV LED, or by any source of germicidal UV light, including a conventional mercury lamp. This is possible because the remote germicidal UV light source 234 is remote from the dental hand tool 104, and thus it is not required to fit within the dental hand tool 104, or operate at voltages safe for use in a dental hand tool 104.

In embodiments where the germicidal UV light source transparent window 224 emits wide angle (non collimated) germicidal UV light, the wide angle germicidal UV light can be substantially collimated using a germicidal UV light transparent plate 216" when that germicidal UV light transparent plate 216" is a quartz collimating lens. Alternatively, the wide angle germicidal UV light can be substantially collimated using a parabolic reflector 230. In such an embodiment, germicidal UV light transparent plate 216" can be a quartz plate that simply allows the already collimated germicidal UV light to pass through it into the disinfection reactor inner chamber 226. However, germicidal UV light transparent plate 216" can also be a quartz lens that further collimates the germicidal UV light emitted by germicidal UV light source transparent window 224.

In embodiments where the germicidal UV light source transparent window 224 emits narrow angle (collimated) germicidal UV light, germicidal UV light transparent plate 216" may be a quartz plate that simply allows the already collimated germicidal UV light to pass through it. However, as before, germicidal UV light transparent plate 216 can also be a quartz lens that further collimates the germicidal UV light emitted by germicidal UV light source transparent window 224.

The present invention will provide excellent disinfection of dental fluid required for dental hand tools. The commonly accepted dosage of germicidal UV light needed to inactivate 99.99% (or "4 log reduction") of most common bacterial and protozoan pathogens is 40 mJ/cm$^2$. This dose is the light irradiance "I" measured in milliwatts per cm$^2$, multiplied by the residence time "t" the dental fluid spends in the reactor. For a UV LED that is capable of emitting 50 mW of germicidal UV light, the intensity can be approximated by the LED power "$P_{LED}$" divided by the reactor cross-sectional area "A". The dose "D" is therefore:

$$D = I*t = (P_{LED}/A)*t.$$

The residence time "t" is also determined by the volume of the reactor "V". In this case, V=A*L, where "L" is the length of the disinfection reactor 106, divided by the water flow through the reactor "F". Therefore, $$t = V/F = (A*L)F.$$

Substituting the expression for t into the first equation gives:

$$D = P_{LED}*L/F, \text{ or}$$

$$F = P_{LED}*L/D.$$

For a desired dose of 40 mJ/cm2 with a germicidal UV LED power of 50 mW, a one centimeter long disinfection reactor inner chamber 226 will yield a maximum flow of 1.25 cm$^3$/sec or 75 cm$^3$/min. This will be an adequate flow of dental fluid to supply a dental hand tool 104, and more powerful LED's will proportionally increase the maximum flow possible with "4 log reduction" of pathogens. A feature of the invention shows an optional disinfection reactor distal end reflective surface 206 on the disinfection reactor distal end 204. This will increase the intensity of the germicidal UV light in the disinfection reactor interior chamber 226 and therefore increase the maximum flow of properly disinfected dental fluid. This invention therefore shows that a miniature UV disinfection reactor 106 can be constructed which has excellent disinfection properties, while being small enough to be incorporated into a dental hand tool.

Any cited references are incorporated herein in their entirety to the extent not inconsistent with the teachings herein. While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A dental hand tool for delivery of disinfected dental fluid under pressure to a dental patient comprising a main body having a main body proximate end, a main body distal end, and at least one conduit associated with the main body proximate end, and a detachable dental utility connector associated with the main body proximate end, the dental utility connector comprising a water supply conduit, an LED power and control conduit, and a disinfection reactor, the disinfection reactor comprising a germicidal UV light source end, a disinfection reactor distal end, and at least one disinfection reactor wall which together with the ends define a confined disinfection reactor inner chamber having a longitudinal axis between the ends, a disinfection reactor fluid inlet on the at least one disinfection reactor wall that receives the dental fluid from the water supply conduit, a disinfection reactor dental fluid outlet on the at least one disinfection reactor wall, and a conduit associated with the dental fluid outlet for delivering dental fluid to the main body proximate end;

wherein the germicidal UV light source end directs germicidal UV light toward the disinfection reactor distal end generally along the longitudinal axis of the chamber, such that collimated germicidal UV light substantially irradiates a substantial portion of the disinfection reactor inner chamber to disinfect the dental fluid just prior to being delivered to the point of use relative to the patient, wherein disinfection of fluid occurs while within the disinfection reactor inner chamber after entering into the disinfection reaction inner chamber through the disinfection reactor fluid inlet and before exiting the disinfection reaction inner chamber through the disinfection reactor fluid outlet; wherein fluid from the disinfection reactor fluid outlet is delivered to the main body distal end and out the main body distal end to point of use; and wherein the germicidal UV light source comprises a UV LED.

2. The dental hand tool of claim 1, wherein the germicidal UV light source end comprises a wide angle germicidal UV light emitting diode, and a quartz collimating lens.

3. The dental hand tool of claim 1, wherein the germicidal UV light source end comprises a wide angle germicidal UV light emitting diode, a germicidal UV light emitting diode power source, a parabolic reflector, and a germicidal UV light transparent plate.

4. The dental hand tool of claim 1, wherein the germicidal UV light source end comprises a narrow angle germicidal UV light emitting diode emitting collimated germicidal UV light.

5. The dental hand tool of claim 4, wherein the germicidal UV light source end further comprises a germicidal UV light transparent plate between the narrow angle germicidal UV light emitting diode and the disinfection reactor.

6. The dental hand tool of claim 4, wherein the germicidal UV light source end further comprises a germicidal UV light transparent quartz lens between the narrow angle germicidal UV tight emitting diode and the disinfection reactor.

7. The dental hand tool of claim 1, wherein the germicidal UV light source end comprises a germicidal UV light emitting diode array.

8. The dental hand tool of claim 1, wherein the germicidal UV light source end comprises a remotely located germicidal UV light source, a germicidal UV light transmitting fiber optic cable, and a quartz collimating lens.

9. The dental hand tool of claim 1, wherein the germicidal UV light source end comprises a remotely located germicidal UV light source, a germicidal UV light transmitting fiber optic cable, a parabolic reflector, and a germicidal UV light transparent plate.

10. The dental hand tool of claim 1, wherein the germicidal UV light source end comprises a remotely located germicidal UV light source, a germicidal UV light transmitting fiber optic cable that transmits the germicidal UV light from the remotely located germicidal UV light source to a germicidal UV light source transparent window that emits collimated germicidal UV light into the disinfection reactor.

11. The dental hand tool of claim 10, wherein the germicidal UV light source end further comprises a germicidal UV light transparent plate between the germicidal UV light source transparent window and the disinfection reactor.

12. The dental hand tool of claim 10, wherein the germicidal UV light source end further comprises a germicidal UV light transparent quartz lens between the germicidal UV light source transparent window and the disinfection reactor.

13. The dental hand tool of claim 1, wherein the germicidal UV light source end comprises a remotely located germicidal UV light source, and a plurality of germicidal UV light transmitting fiber optic cables, wherein germicidal UV light transmitting fiber optic cable emitting ends form a germicidal UV light transmitting fiber optic cable array.

14. The dental hand tool of claim 1, wherein the disinfection reactor is elongated along the germicidal UV light path.

15. The dental hand toot of claim 1, wherein the disinfection reactor is integral to a dental utility conduit connector that connects the dental utility conduit to the main body proximate end.

16. The dental hand tool of claim 1, wherein the disinfection reactor distal end further comprises a germicidal UV light sensor and germicidal UV light sensor monitor to monitor an intensity of the germicidal UV light in the disinfection reactor inner chamber.

17. The dental hand tool of claim 1, wherein the disinfection reactor is constructed of material that will conduct heat from a germicidal UV light source to the dental fluid.

18. The dental hand tool of claim 1, wherein the disinfection reactor distal end comprises a reflective surface and/or a surface with a reflective coating such that it reflects the collimated germicidal UV light.

19. The dental hand tool of claim 1, wherein the disinfection reactor walls are at least one of polished and coated in order to reflect the germicidal UV light.

20. The dental hand tool of claim 1, wherein at least one of the germicidal UV light source end and the disinfection reactor distal end are removable from the disinfecting reactor.

21. The dental hand tool of claim 1, wherein the dental utility connector further comprises a dental utility return conduit.

22. A dental delivery system for delivering disinfected dental fluid under pressure to a dental patient comprising a workstation for holding at least one dental hand tool, the dental hand tool comprising a main body having a main body proximate end, a main body distal end, and at least one conduit associated with the main body proximate end, and a detachable dental utility connector associated with the main body proximate end, the dental utility connector comprising a water supply conduit, an LED power and control conduit, a disinfection reactor, the disinfection reactor comprising a germicidal UV light source end, a disinfection reactor distal end, and at least one disinfection reactor wall Which together with the ends define a disinfection reactor inner chamber having a longitudinal axis between the ends, a disinfection reactor fluid inlet on the at least one disinfection reactor wall that receives the dental fluid from the water supply conduit, a disinfection reactor dental fluid outlet on the at least one disinfection reactor wall, and a conduit associated with the dental fluid outlet for delivering dental fluid to the main body proximate end;

wherein the germicidal UV light source end directs germicidal UV light toward the disinfection reactor distal end generally along the longitudinal axis of the chamber, such that collimated germicidal UV light substantially irradiates a substantial portion of the disinfection reactor inner chamber to disinfect the dental fluid just prior to being delivered to the point of use relative to the patient, wherein disinfection of fluid occurs while within the disinfection reactor inner chamber after entering into the disinfection reaction inner chamber through the disinfection reactor fluid inlet and before exiting the disinfection reaction inner chamber through the disinfection reactor fluid outlet; wherein fluid from the disinfection reactor fluid outlet is delivered to the main body distal end and out the main body distal end to point of use; and wherein the germicidal UV light source comprises a UV LED.

23. The dental system of claim 22, herein the dental y connector further comprises a dental utility return conduit.

* * * * *